United States Patent
Minoguchi et al.

(10) Patent No.: US 7,824,388 B2
(45) Date of Patent: Nov. 2, 2010

(54) TAMPON HAVING AN ANGLED FINGER COVER

(75) Inventors: Ryo Minoguchi, Cincinnati, OH (US); Ricky Alan Pollard, Moscow, OH (US); Letha Margie Hines, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 516 days.

(21) Appl. No.: 11/525,730

(22) Filed: Sep. 22, 2006

(65) Prior Publication Data

US 2008/0077108 A1  Mar. 27, 2008

(51) Int. Cl.
*A61F 13/15* (2006.01)
*A61F 13/20* (2006.01)

(52) U.S. Cl. .............. 604/385.15; 604/385.17

(58) Field of Classification Search ............ 604/385.18, 604/904, 385.17
See application file for complete search history.

(56) References Cited

U.S. PATENT DOCUMENTS

| | | | |
|---|---|---|---|
| 3,738,364 A | 6/1973 | Brien et al. | |
| 3,863,636 A | 2/1975 | Johnson | |
| 4,318,407 A * | 3/1982 | Woon | 604/374 |
| 5,370,633 A | 12/1994 | Villalta | |
| 5,891,123 A | 4/1999 | Balzar | |
| 5,911,712 A | 6/1999 | Leutwyler et al. | |
| 6,283,952 B1 | 9/2001 | Child et al. | |
| 6,840,927 B2 * | 1/2005 | Hasse et al. | 604/385.18 |
| 6,932,805 B2 | 8/2005 | Kollwitz et al. | |
| 6,953,456 B2 | 10/2005 | Fuchs et al. | |
| 2004/0049167 A1 | 3/2004 | Hasse et al. | |
| 2004/0199137 A1 | 10/2004 | Lamb | |

FOREIGN PATENT DOCUMENTS

| | | |
|---|---|---|
| DE | 296 20 118 U1 | 3/1998 |
| DE | 201 15 829 U1 | 1/2002 |
| GB | 2 227 666 | 8/1990 |
| JP | 2003-180741 | 7/2003 |
| WO | WO 2005/058219 | 6/2005 |

OTHER PUBLICATIONS

PCT International Search Report dated Mar. 19, 2008.

* cited by examiner

*Primary Examiner*—Melanie J Hand
(74) *Attorney, Agent, or Firm*—Amanda T. Barry (57) ABSTRACT

A digital tampon including an angled finger cover. The tampons can comprise an absorbent mass having an insertion end and a withdrawal end and an angled finger cover.

18 Claims, 4 Drawing Sheets

TAMPON HAVING AN ANGLED FINGER COVER

FIELD OF THE INVENTION

The invention relates to digital tampons and more particularly to digital tampons having angled finger covers.

BACKGROUND OF THE INVENTION

Catamenial tampons are typically inserted into a vagina of a woman to absorb menstrual discharges during menstruation. Such tampons are generally inserted either with the aid of an applicator or digitally via a user's finger.

In the case of a digital tampon that is inserted into the vagina by hand, the user is at risk of contaminating their fingers and/or nails with menstrual discharge during insertion. In addition, a user can risk damaging and/or infecting the vagina during insertion due to contact between the vagina and the user's finger and nail. Thus, some digital tampons can include a portion that can cover a user's finger and nail to promote clean and hygienic insertion. Known coverings, however, can be difficult to deploy and use.

Digital tampons are generally tightly packed in individual wrappers to make the tampon easy to carry and to protect the tampon from the environment prior to use. Digital tampons with finger covers typically require the finger cover to be folded and/or compacted so that the cover can fit in the wrapper. When the user opens and removes the wrapper to prepare the tampon for insertion, the finger cover can remain compacted and/or can be tangled. The user may have to expand the finger cover and search for the opening in the cover in order to insert a finger. This procedure can also disrupt hygienic tampon handling due to the user touching the tampon body with fingers while the user tries to expand the finger cover and locate its opening.

As such, it would be desirable to provide a digital tampon having a finger cover with improved ease of deployment. It would also be desirable to provide a digital tampon having a finger cover with improved ease of use.

SUMMARY OF THE INVENTION

Tampons comprising a finger cover are provided. The tampons can comprise an absorbent mass having an insertion end and a withdrawal end and an angled finger cover, such as, e.g., a finger cover that can have an angled opening. The tampons can also include one or more withdrawal cords that can be joined to the finger cover, such as, e.g., at one or more cover joints. The withdrawal end can include a cavity that can be open to the withdrawal end. At least a portion of the finger cover and/or withdrawal cord can be at least partially disposed in the withdrawal end of the tampon.

DETAILED DESCRIPTION OF THE INVENTION

The present invention relates to tampons that include an angled finger cover. The finger cover can have an angled opening, such as, e.g., an opening that can be formed at an angle. In certain embodiments, the finger cover can have improved ease of deployment and opening for use. The finger cover can be adapted to provide convenient and hygienic preparation of the finger cover when the tampon is prepared for insertion into the body. The finger cover can also protect the user's finger and/or body from contamination or injury. Furthermore, the improved ease of use can promote use of a tampon including a finger cover, such that more users can experience increased hygienic and health benefits that can be associated with finger cover use.

In certain embodiments, the tampon can comprise one or more withdrawal cords. The withdrawal cord can be joined to the withdrawal end of the tampon. One or more withdrawal cords can extend from the withdrawal end of the tampon and can be joined to the finger cover at one or more cover joints.

The tampon can include a wrapper. When the tampon includes a wrapper, the finger cover and/or the withdrawal cord can be compacted in a suitable manner. For example, the finger cover and/or withdrawal cord can be folded, rolled, wound, looped, twisted, and or otherwise compacted such that at least a portion of, a majority of, and/or all of the finger cover and/or withdrawal cord can fit in the wrapper. In certain embodiments, the finger cover and/or withdrawal cord are packed such that at least a portion of the withdrawal cord is visible upon opening the wrapper. When the wrapper is opened and at least a portion of the wrapper is removed, the user can hold the end of the withdrawal cord visible at the withdrawal end of the tampon and can pull the withdrawal cord to extend it, expanding the finger cover. In certain embodiments, an opening for finger insertion can be visible upon expansion of the finger cover. Alternatively, or in addition, the withdrawal cord can be joined to the wrapper such that the withdrawal cord is pulled and/or the finger cover is expanded when the wrapper is opened and/or at least a portion and/or all of the wrapper is discarded.

A portion of the withdrawal cord can be joined with a portion of the wrapper so that the withdrawal cord and the finger cover can be automatically deployed when all or a part of the wrapper is opened and removed. In certain embodiments, the withdrawal cord can be joined to the wrapper at one or more wrapper joints. A joint between the end of the withdrawal cord and the wrapper, i.e., a wrapper joint, can have sufficient strength such that the joint is maintained during the deployment of the finger cover, yet breaks off after deployment, for example, when the withdrawal cord and/or finger cover is at least partially extended. In certain embodiments, the joint can break off when the withdrawal cord and/or finger cover is fully extended.

The wrapper can separate into two or more pieces, such as, e.g., at least a piece covering the withdrawal end and/or a piece covering the insertion end. In certain embodiments, the wrapper can have a design that opens about the withdrawal end, allowing the withdrawal end to be exposed while other portions of the tampon remain enclosed in the wrapper. In certain embodiments, the user can open the wrapper proximate to the withdrawal end and pull the end of the withdrawal cord located there to expand the finger cover while the insertion end of the tampon remains wrapped. The user can hold the wrapped portion of the tampon without fear of contamination while the user deploys the finger cover and inserts her finger. In certain embodiments, when the user opens and removes at least a portion of, a majority of, and/or all of the wrapper proximate to the withdrawal end, the withdrawal cord and/or the finger cover can automatically deploy.

In certain embodiments, the tampon can include a cavity open to the withdrawal end of the tampon. The finger cover can be at least partially disposed in the cavity. A portion of the cord can also be contained in the cavity. In certain embodiments, a portion of the cord can be visible at the withdrawal end of the tampon. By drawing the cord out of the cavity, the user can displace and expand the finger cover, for example, such that it has a clear opening for finger insertion. The cavity in the withdrawal end can provide a pocket to accommodate the user's finger, such as, e.g., a pocket that can provide improved grip and/or steering of the tampon during insertion into the body.

As used herein, the term "tampon" refers to any type of absorbent structure, such as an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

The term "digital tampon" refers to a tampon which is intended to be inserted into the vaginal canal with the user's finger and generally without the aid of an applicator.

The term "insertion end" refers to the end of the tampon that is intended to enter the vaginal canal first when inserting the tampon.

As used herein, the term "withdrawal end" refers to the end of the tampon opposite the insertion end and that is intended to exit the vaginal canal first when the tampon is removed from the vagina.

As used herein, the term "asymmetric insertion end" refers to an insertion end of a tampon that is asymmetric about the X axis.

As used herein, the term "X axis" refers to an axis in a tampon that has a direction generally aligned with a direction of insertion of the tampon and that includes a geometric centroid of the tampon (i.e., a longitudinal "center line" in the tampon).

Figure 1:
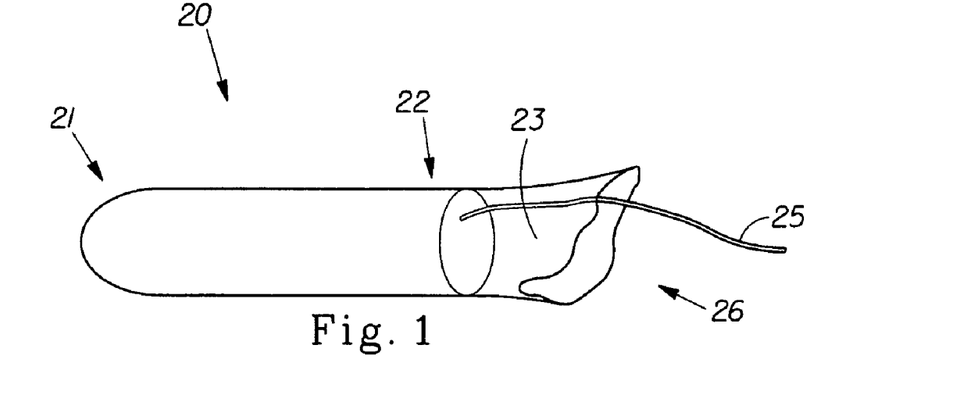
FIG. 1 is a perspective view of one embodiment of the present invention.

FIG. 1 shows one embodiment of the tampon 20 of the present invention. The tampon 20 has an insertion end 21 and a withdrawal end 22. As shown in FIG. 1, the finger cover 23 can extend from the withdrawal end 22 of the tampon 20. The withdrawal cord 25 can extend from the withdrawal end 22 of the tampon 20. The finger cover 23 can form an opening 26 for a user's finger. The opening 26 can be angled.

Figure 2:
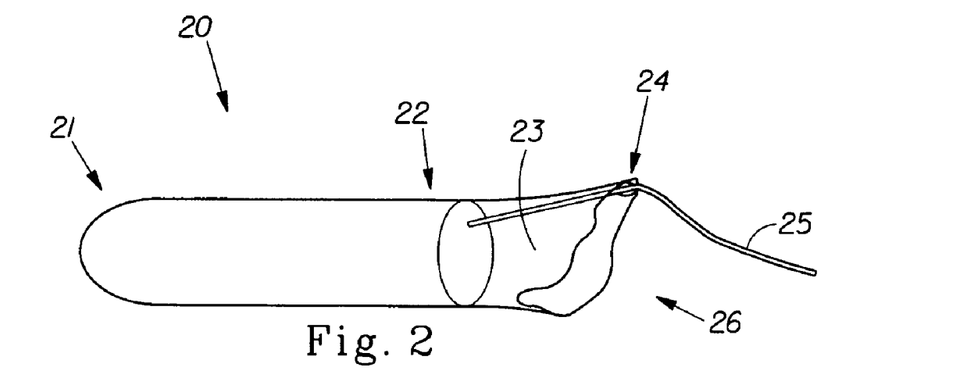
FIG. 2 is a perspective view of one embodiment of the present invention.

FIG. 2 shows one embodiment of the tampon 20 of the present invention. The tampon 20 has an insertion end 21 and a withdrawal end 22. As shown in FIG. 2, the finger cover 23 can extend from the withdrawal end 22 of the tampon 20. The tampon 20 can have a withdrawal cord 25 that extends from the withdrawal end 22 of the tampon 20 and that attaches to the finger cover 23 at a cover joint 24. The finger cover 23 can form an opening 26 for a user's finger. The opening 26 can be angled.

Figure 3:
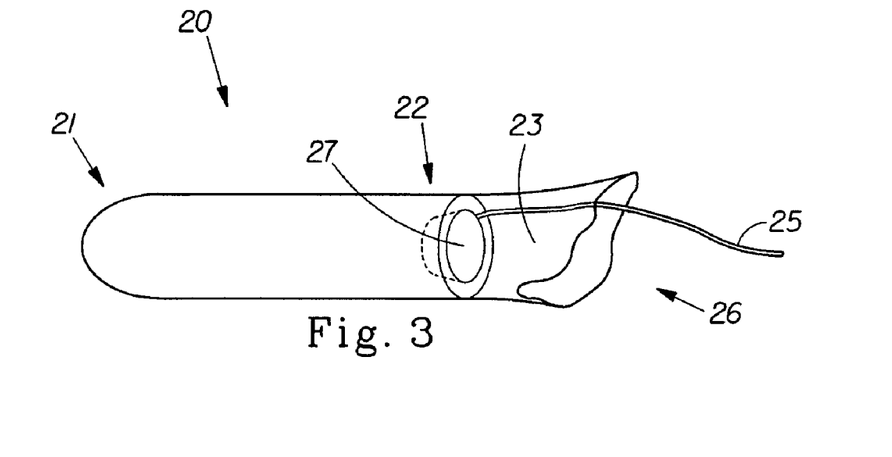
FIG. 3 is a perspective view of one embodiment of the present invention.

FIG. 3 shows one embodiment of the tampon 20 of the present invention. The tampon 20 has an insertion end 21 and a withdrawal end 22. As shown in FIG. 3, the finger cover 23 can extend from the withdrawal end 22 of the tampon 20. The withdrawal cord 25 can extend from the withdrawal end 22 of the tampon 20. The tampon can have a cavity 27 at the withdrawal end 22 of the tampon 20 that can be suitable for use as a finger pocket. The finger cover 23 can form an opening 26 for a user's finger. The opening 26 can be angled.

Figure 4:
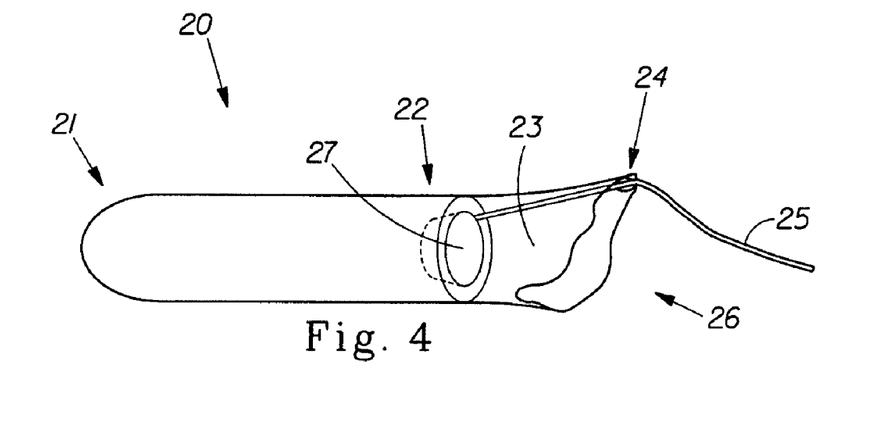
FIG. 4 is a perspective view of one embodiment of the present invention.

FIG. 4 shows one embodiment of the tampon 20 of the present invention. The tampon 20 has an insertion end 21 and a withdrawal end 22. As shown in FIG. 4, the finger cover 23 can extend from the withdrawal end 22 of the tampon 20. The withdrawal cord 25 can extend from the withdrawal end 22 of the tampon 20 and can attach to the finger cover 23 at a cover joint 24. The tampon can have a cavity 27 at the withdrawal end 22 of the tampon 20 that can be suitable for use as a finger pocket. The finger cover 23 can form an opening 26 for a user's finger. The opening 26 can be angled.

Figure 5:
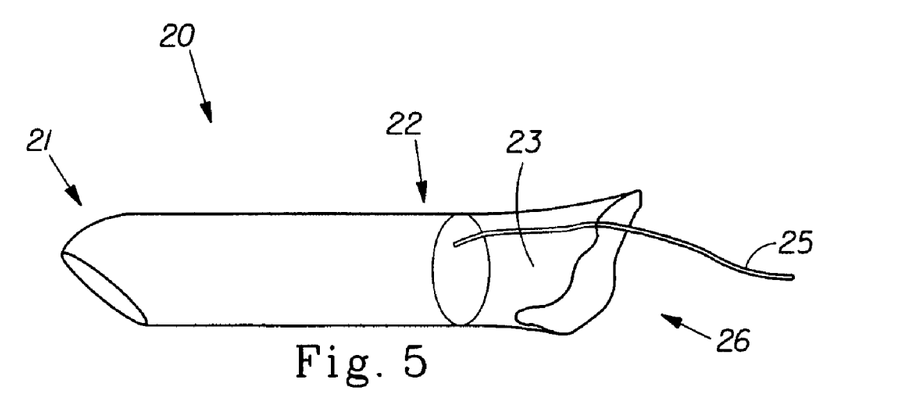
FIG. 5 is a perspective view of one embodiment of the present invention.

FIG. 5 shows one embodiment of the tampon 20 of the present invention. The tampon 20 has an insertion end 21 that can be asymmetric and a withdrawal end 22. As shown in FIG. 5, the finger cover 23 can extend from the withdrawal end 22 of the tampon 20. The withdrawal cord 25 can extend from the withdrawal end 22 of the tampon 20. The finger cover 23 can form an opening 26 for a user's finger. The opening 26 can be angled.

Figure 6:
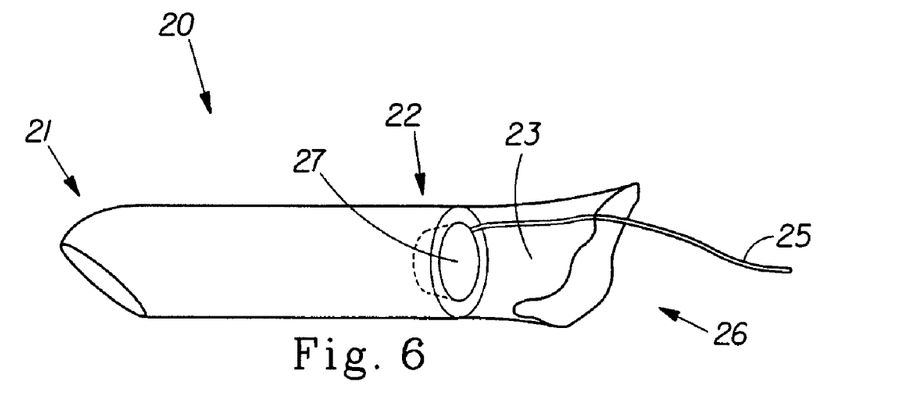
FIG. 6 is a perspective view of one embodiment of the present invention.

FIG. 6 shows one embodiment of the tampon 20 of the present invention. The tampon 20 has an insertion end 21 and a withdrawal end 22. As shown in FIG. 6, the finger cover 23 can extend from the withdrawal end 22 of the tampon 20. The withdrawal cord 25 can extend from the withdrawal end 22 of the tampon 20. The tampon can have a cavity 27 at the withdrawal end 22 of the tampon 20 that can be suitable for use as a finger pocket. The finger cover 23 can form an opening 26 for a user's finger. The opening 26 can be angled.

Figure 7:
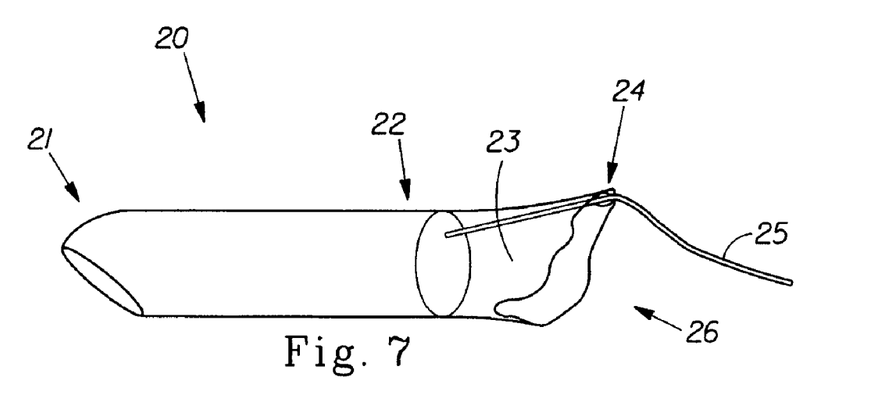
FIG. 7 is a perspective view of one embodiment of the present invention.

FIG. 7 shows one embodiment of the tampon 20 of the present invention. The tampon 20 has an insertion end 21 and a withdrawal end 22. As shown in FIG. 7, the finger cover 23 can extend from the withdrawal end 22 of the tampon 20. The withdrawal cord 25 can extend from the withdrawal end 22 of the tampon 20 and can attach to the finger cover 23 at a cover joint 24. The finger cover 23 can form an opening 26 for a user's finger. The opening 26 can be angled.

Figure 8:
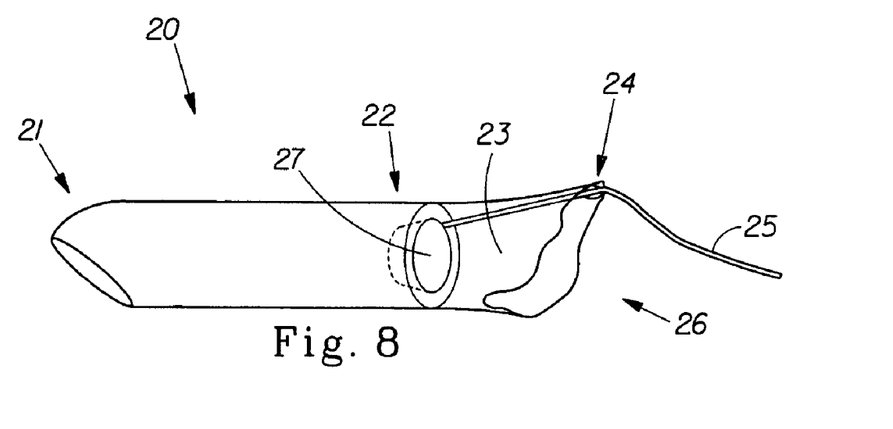
FIG. 8 is a perspective view of one embodiment of the present invention.

FIG. 8 shows one embodiment of the tampon 20 of the present invention. The tampon 20 has an insertion end 21 and a withdrawal end 22. As shown in FIG. 8, the finger cover 23 can extend from the withdrawal end 22 of the tampon 20. The withdrawal cord 25 can extend from the withdrawal end 22 of the tampon 20 and can attach to the finger cover 23 at a cover joint 24. The tampon can have a cavity 27 at the withdrawal end 22 of the tampon 20 that can be suitable for use as a finger pocket. The finger cover 23 can form an opening 26 for a user's finger. The opening 26 can be angled.

The finger cover can be formed from any suitable material. In certain embodiments, the finger cover can be formed as an extension of one or more components or of a portion of one or more components of the tampon, such as, e.g., the overwrap and/or the absorbent mass. Alternatively, or in addition, the finger cover can be added as a separate material and joined to the tampon, such as, e.g., at the withdrawal end of the tampon.

In certain embodiments, the finger cover can be formed as an extension of the tampon overwrap. The overwrap can be any suitable material, such as, e.g., a nonwoven or a film that allows the passage of fluid when positioned over the tampon, such as, for example, due to apertures and/or hydrophilic zones present in a hydrophobic surface. In certain embodiments, the overwrap material can prevent fluid passage when used as a finger cover.

The finger cover can also or alternatively be added as a separate material joined with the tampon. The finger cover can include one or more materials that can be a nonwoven or film, such as, e.g., a nonwoven or film that is fluid impervious and/or fluid repellent. When the tampon comprises an overwrap, the finger cover can be joined with the overwrap covering the tampon. In certain embodiments, at least a portion of the material of the finger cover can cover at least a portion of the withdrawal end of the tampon. Extension of the finger cover material over at least a portion of the withdrawal end of the tampon can provide a fluid masking effect that can provide the user with a perception of a tampon comprising a white end after use, such as, e.g., when the finger cover comprises one or more fluid impervious materials.

The finger cover can have any suitable shape and dimension. The finger cover can comprise an opening, such as an opening intended for the insertion of a user's finger. In certain embodiments, the opening can be angled, such as, e.g., formed at an angle. For example, the opening can be angled with respect to a longitudinal axis in the tampon. In certain embodiments, the opening can be angled so that the user can easily adjust the finger during insertion of the tampon, while maintaining the fit between the finger and the finger cover. An angled opening can be beneficial for facilitating expansion of the finger cover, easier location of the opening for insertion of the finger, and for wearing comfort.

In certain embodiments, an angled opening can enable consistent orientation of the insertion end of the tampon during insertion, such as, for example, when the tampon includes an asymmetric insertion end. The asymmetric insertion end of the tampon can include a angled side, such as, e.g., a side that has a smaller angle to the X axis than any other side of the insertion end, and/or a side comprising a face that is at an angle to the X axis. The portion of the finger cover of the opening of the finger cover proximal to the withdrawal end can be generally aligned with angled side of the asymmetric insertion end such that when the user orients a finger in the finger cover and inserts the tampon into the vagina, the angled side of the insertion end can face the superior surface of the vagina and provide smoother insertion and improved placement and fluid interception by the tampon in the vagina.

The opening can be angled at any suitable angle. In certain embodiments, the opening can be angled with respect to a longitudinal axis of the tampon, such as, e.g., the X axis of the tampon. In certain embodiments, the angle of the finger cover can be defined as an angle formed between a vector that is parallel to the X axis of the tampon and directed from the insertion end to the withdrawal end, and a vector that is directed from a point on the edge of the opening of the finger cover proximal to the withdrawal end to a point on the edge of the opening of the finger cover distal to the withdrawal end. Suitable angles can be, for example, less than about 90 degrees, less than about 80 degrees, less than about 70 degrees, or any other suitable angle.

The finger cover can be angled in any suitable manner, such as, e.g., by cutting, shaping, and/or otherwise forming the finger cover. In certain embodiments, the finger cover can be angled before attachment to the tampon. Alternatively, or in addition, the finger cover can be angled after attachment to the tampon.

As discussed herein, the tampon can comprise one or more withdrawal cords. The one or more withdrawal cords can extend from the withdrawal end of the tampon and can be joined to the finger cover at one or more cover joints. The one or more joints between the finger cover and the withdrawal cord, i.e., one or more cover joints, can be formed by any method suitable for joining such materials. Suitable methods, include, e.g., fusion, heat bond, welding, adhesive, stitching, entangling, riveting, staple, hook, ball and ring, and/or any other suitable method. The cover joint can be adapted such that a force from the withdrawal cord is applied to the finger cover only in the event that the withdrawal cord is pulled. In certain embodiments, the withdrawal cord can be formed as part of the finger cover, such as, e.g., as an extension of the finger cover. The withdrawal cord can also or alternatively extend from the finger cover. Withdrawal cords useful in the present invention can be made of any suitable material, such as, e.g., cotton and rayon. In certain embodiments, the withdrawal cord can be made of the same material as the finger cover.

In certain embodiments, the finger cover can have a maximum length such that the finger cover covers the user's finger sufficiently while the tampon is inserted into the body and/or does not cause any discomfort while the tampon is worn by the user. The maximum length can be, for example, less than about 70 mm, between about 10 mm and about 60 mm, between about 20 mm and about 50 mm, or any other suitable length. In certain embodiments, the finger cover can include a tab that substantially faces a palm side of the finger placed on the tampon so that the user can stably hold the tampon by pinching the tab until the tampon enters the body.

The tampon's total length can be measured from the insertion end to the withdrawal end along the direction of insertion. In certain embodiments, a typical compressed tampon for human use is generally about 10 to about 16 mm wide and about 30 to about 60 mm long, often depending on absorbency, but can be any suitable width and length. For other mammals, typical tampon dimensions can vary based on differences in their particular vaginal canal geometry.

The tampon and any component thereof can comprise a pledget that can include a single material or a combination of materials. The materials for the tampon can be formed into a fabric, web, or batt that is suitable for use in the tampon by any suitable process such as, for example, airlaying, carding, wetlaying, hydroentangling, or other known techniques.

The pledget can be constructed from a wide variety of liquid-absorbing materials commonly used in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, stiperabsorbent materials, such as superabsorbent polymers or absorbent gelling materials can be incorporated into the tampon.

The pledget can be any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911,712; 6,740,070; 6,887,266; and 6,953,456.

In certain embodiments, all or a portion of the tampon can be compressed into a substantially cylindrical configuration, however, other shapes are possible. These can include shapes having a cross section or cross-section element that can be described as rectangular, triangular, trapezoidal, semi-circular, hourglass, or other suitable shapes.

In certain embodiments, the tampon can be a tampon having a radially compressed rolled construction. The tampon can be constructed by rolling and radially compressing a pledget. The pledget can be rolled around a mandrel then compressed with or without the mandrel. In certain embodiments, a cavity left behind after the mandrel is removed can provide a finger pocket. The tampon can also be constricted by pressing a pledget, such as, for example, a cylindrical pledget, in forming dies with a pushrod. A cavity that can be a finger pocket can be formed in part of the blank pressed against a convex in the forming dies or the pushrod. The withdrawal cord can be at least partially disposed in the cavity before compression. In certain embodiments, at least a portion of the withdrawal cord can stick out of and/or be visible at the withdrawal end of the tampon. II certain embodiments, the user can pull the withdrawal cord to extend the withdrawal cord and/or the user can remove at least a portion of the wrapper joined with the withdrawal cord such that the finger pocket can spontaneously open.

The cavity can be any suitable size. Suitable sizes include, for example, a size appropriate for containing at least a portion of the finger cover and/or at least a portion of the withdrawal cord and/or a size appropriate for positioning a portion of a user's finger within the cavity. In certain embodiments, the cavity can be sized to contain the entire finger cover. The cavity can have a diameter that is the same as or less than the diameter of the withdrawal edge of the tampon. For example, the cavity can have a diameter that is about 90%, about 80%, about 70%, about 60%, about 50%, or less, of the diameter of the withdrawal edge of the tampon.

The depth of the cavity can be any depth suitable for containing at least a portion of the finger cover and/or at least a portion of the withdrawal cord and/or suitable for positioning of a portion of a user's finger within the cavity. Suitable depths include, for example, about 5 mm, about 10 mm, about 15 mm, or any other suitable depth.

The tampon can also or alternatively include one or more overwraps. The overwrap can be any suitable material, such as, for example, rayon, cotton, bicomponent fibers, polyethylene, polypropylene, other suitable natural or synthetic fibers known in the art, and mixtures thereof. In certain embodiments, the tampon can comprise an overwrap material that substantially encloses the compressed tampon. The tampon can also or alternatively include a secondary absorbent member, such as, for example, a mass of secondary absorbent material attached to the withdrawal cord proximate the withdrawal end of the tampon. Suitable secondary absorbent members are described in, e.g., U.S. Pat. No. 6,258,075.

The tampons can optionally employ wrappers that conform to the outer surface of the tampon in order to visually show the consumer the tampons packaged therein. Such wrappers are particularly useful when the tampons are intended to be used digitally and/or are not housed in an applicator prior to use.

The wrappers can substantially enclose each individual tampon and can be removed prior to insertion and use. In certain embodiments, the wrappers can comprise one or more portions.

Wrappers can be made in any suitable manner. The wrapper material used can be any material suitable to be used for hygienically wrapping tampons. Suitable wrapper materials include, e.g., polymeric films made of polyethylene, polypropylene, polyester, polystyrene, PET (polyethylenetherephithalate), cellophane, polyamide, poly(vinyl chloride), ethylene-viniyl acetate copolymer and the like; synthetic or natural (e.g. rubber) elastomers; generally occlusive materials such as metallic foils (e.g. aluminum foil); non-occlusive or porous materials, such as nonwovens, wovens, scrims, meshes and papers; or any other suitable materials. The wrapper can comprise one or more flexible polymeric films, such as, for example, films having a thickness of less than about 11 m. Wrappers can be made and applied to the tampon using any suitable technique, including, for example, heat-shrinking, heat sealing, adhesives, pressure, stretching, lamination, coating, gluing, embossing, crimping, sewing, stitching, entangling, mechanical interlocking, cold pressure welding, ultrasonic bonding, and/or combinations thereof.

Wrappers can be provided with an opening means comprising at least one line of weakness. This opening means can prevent or reduce separation of the wrapper into more than one piece of wrapper material upon opening of the wrapper. For instance, the line of weakness can only extend around a portion of the wrapped tampon in terms of length and perimeter in order to prevent tearing-off of parts of the wrapper upon opening of the wrapper, which could result in fragmentation of the wrapper.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital tampon comprising an absorbent mass having an insertion end and a withdrawal end and a finger cover comprising an angled opening, wherein the opening is angled less than about 80 degrees with respect to a longitudinal axis of the tampon.

2. The tampon of claim 1, wherein the withdrawal end includes a cavity open to the withdrawal end.

3. The tampon of claim 2, wherein at least a portion of the finger cover is at least partially disposed in the cavity.

4. The tampon of claim 1, wherein the tampon further comprises one or more withdrawal cords.

5. The tampon of claim 4, wherein the withdrawal end includes a cavity open to the withdrawal end and wherein at least a portion of the finger cover and at least a portion of the one or more withdrawal cords are at least partially disposed within the cavity.

6. The tampon of claim 5, wherein the finger cover is adapted to be at least partially displaced out of the cavity by at least partially extending the one or more withdrawal cords.

7. The tampon of claim 4, wherein the one or more withdrawal cords are formed as an extension of the finger cover.

8. The tampon of claim 1, wherein the tampon comprises one or more overwraps that extend from the withdrawal end of the tampon to form the finger cover.

9. The tampon of claim 1, wherein the finger cover is joined to the withdrawal end of the tampon.

10. A digital tampon comprising an absorbent mass having an insertion end and a withdrawal end and a finger cover comprising an angled opening, wherein the insertion end is asymmetric around an X axis of the tampon.

11. The tampon of claim 10, wherein the insertion end of the tampon includes one or more sides that are at an angle to the X axis, and wherein at least a portion of the opening of the finger cover proximal to the withdrawal end is generally aligned with one of the sides.

12. The tampon of claim 10, wherein the opening is angled with respect to a longitudinal axis of the tampon.

13. The tampon of claim 10, wherein the opening is angled less than about 90 degrees, less than about 80 degrees and/or less than about 70 degrees.

14. A digital tampon comprising an absorbent mass having an insertion end and a withdrawal end, a finger cover comprising an angled opening, and at least one withdrawal cord joined to the finger cover at one or more cover joints, wherein the tampon is at least partially enclosed by at least one wrapper, and wherein at least one of the withdrawal cords is joined to at least one of the wrappers at one or more wrapper joints.

15. The tampon of claim 14, wherein the wrapper comprises two or more pieces.

16. The tampon of claim 14, wherein the withdrawal cord is adapted to be at least partially extended when at least a portion of the wrapper is removed.

17. The tampon of claim 14, wherein the finger cover is adapted to be deployed when at least a portion of the wrapper is removed.

18. The tampon of claim 14, wherein the wrapper joint is adapted to break to separate the wrapper and withdrawal cord when the withdrawal cord is at least partially extended.

* * * * *

UNITED STATES PATENT AND TRADEMARK OFFICE
CERTIFICATE OF CORRECTION

PATENT NO.       : 7,824,388 B2
APPLICATION NO.  : 11/525730
DATED            : November 2, 2010
INVENTOR(S)      : Minoguchi et al.

It is certified that error appears in the above-identified patent and that said Letters Patent is hereby corrected as shown below:

Column 5

Line 59, delete "proximal" and insert --distal--.

Line 61, delete "distal" and insert --proximal--.

Column 6

Line 65, delete "stiperabsorbent" and insert --superabsorbent--.

Column 7

Line 21, delete "constricted" and insert --constructed--..

Line 29, delete "II" and insert --In--.

Signed and Sealed this
Twenty-ninth Day of November, 2011

David J. Kappos
*Director of the United States Patent and Trademark Office*